US010610268B2

(12) United States Patent
Barry et al.

(10) Patent No.: US 10,610,268 B2
(45) Date of Patent: Apr. 7, 2020

(54) ANCHOR AND ROD CONNECTOR

(71) Applicant: Zimmer Biomet Spine, Inc., Westminster, CO (US)

(72) Inventors: David Barry, Teaneck, NJ (US); Oliver Buchert, Franklin Lakes, NJ (US); Michal Zentko, Cherry Hill, NJ (US); Mary Beth Grabowsky, Roseland, NJ (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 15/952,028

(22) Filed: Apr. 12, 2018

(65) Prior Publication Data
US 2018/0228521 A1  Aug. 16, 2018

Related U.S. Application Data

(63) Continuation of application No. 14/556,902, filed on Dec. 1, 2014, now Pat. No. 9,980,757.

(51) Int. Cl.
*A61B 17/70* (2006.01)
*A61B 17/16* (2006.01)

(52) U.S. Cl.
CPC ........ *A61B 17/7079* (2013.01); *A61B 17/705* (2013.01); *A61B 17/7014* (2013.01); *A61B 2017/1602* (2013.01)

(58) Field of Classification Search
CPC ...................................... A61B 17/7049–7052
USPC .................................................. 606/278, 260
See application file for complete search history.

(56) References Cited

U.S. PATENT DOCUMENTS

| 9,980,757 | B2 | 5/2018 | Barry et al. |
| 2002/0095153 | A1 | 7/2002 | Jones et al. |
| 2006/0009777 | A1 | 1/2006 | Lim et al. |
| 2006/0111715 | A1 | 5/2006 | Jackson |
| 2006/0229611 | A1* | 10/2006 | Avery ................ A61B 17/7011 606/260 |
| 2008/0027436 | A1 | 1/2008 | Cournoyer et al. |
| 2010/0121385 | A1 | 5/2010 | Blain et al. |
| 2012/0271353 | A1* | 10/2012 | Barry ................ A61B 17/7014 606/258 |
| 2013/0150889 | A1 | 6/2013 | Fening et al. |
| 2014/0066989 | A1 | 3/2014 | Mundis et al. |

(Continued)

OTHER PUBLICATIONS

"U.S. Appl. No. 14/556,902, Examiner Interview Summary dated Sep. 29, 2017", 3 pgs.

(Continued)

*Primary Examiner* — Nicholas J Plionis
(74) *Attorney, Agent, or Firm* — Schwegman Lundberg & Woessner, P.A.

(57) ABSTRACT

A method of adjusting a distance between a first surgical rod and a second surgical rod includes providing a surgical rod connector having a housing with first and second ends and a longitudinal passage extending between the first end and the second end. The method also includes positioning the first surgical rod in the first end and positioning the second surgical rod in the second end. The method further includes mounting an anchor mechanism to the surgical rod connector and applying a force on the anchor mechanism and a corresponding force on one of the first and second surgical rods to distract the first and second surgical rods relative to one another.

18 Claims, 14 Drawing Sheets

(56) References Cited

U.S. PATENT DOCUMENTS

2014/0135855 A1    5/2014   Jones et al.
2014/0277170 A1    9/2014   Barrett et al.
2016/0151093 A1    6/2016   Barry et al.

OTHER PUBLICATIONS

"U.S. Appl. No. 14/556,902, Final Office Action dated Feb. 7, 2017", 13 pgs.
"U.S. Appl. No. 14/556,902, Non Final Office Action dated Jun. 27, 2017", 15 pgs.
"U.S. Appl. No. 14/556,902, Non Final Office Action dated Jul. 28, 2016", 12 pgs.
"U.S. Appl. No. 14/556,902, Notice of Allowance dated Jan. 11, 2018", 10 pgs.
"U.S. Appl. No. 14/556,902, Response filed Apr. 21, 2017 to Final Office Action dated Feb. 7, 2017", 18 pgs.
"U.S. Appl. No. 14/556,902, Response filed Sep. 27, 2017 to Non Final Office Action dated Jun. 27, 2017", 11 pgs.
"U.S. Appl. No. 14/556,902, Response filed Oct. 26, 2016 to Non Final Office Action dated Jul. 28, 2016", 21 pgs.
"European Application Serial No. 15197390.6, Extended European Search Report dated Sep. 14, 2016", 8 pgs.
"European Application Serial No. 15197390.6, Response filed Apr. 12, 2017 to Extended European Search Report dated Sep. 14, 2016", 14 pgs.

\* cited by examiner

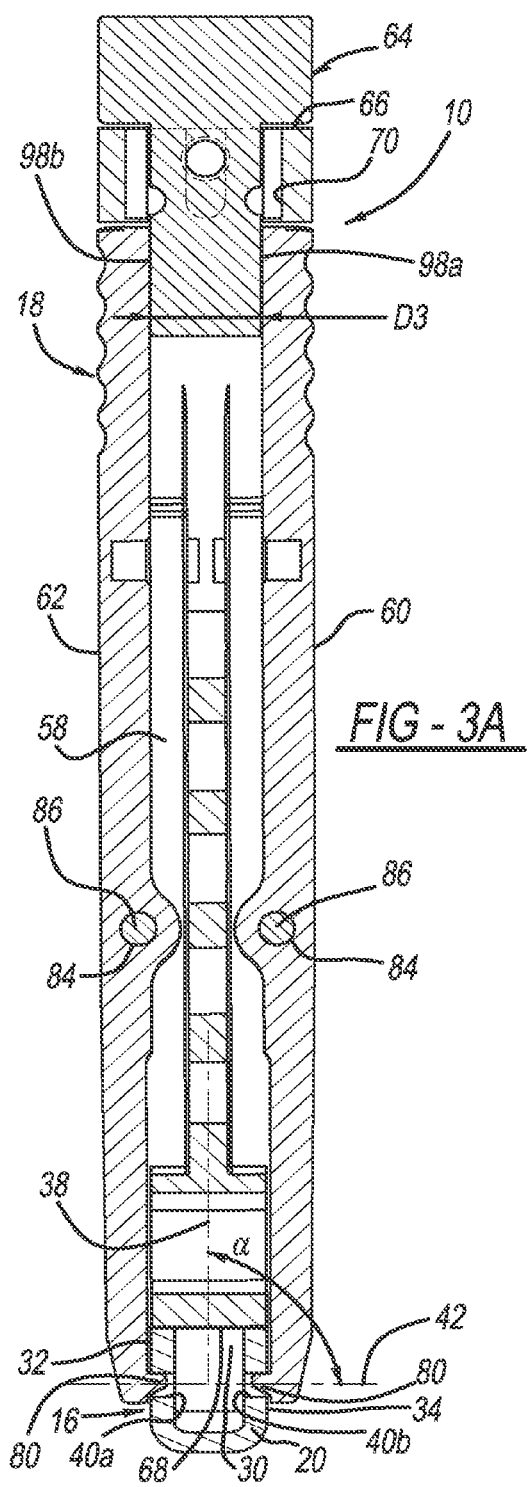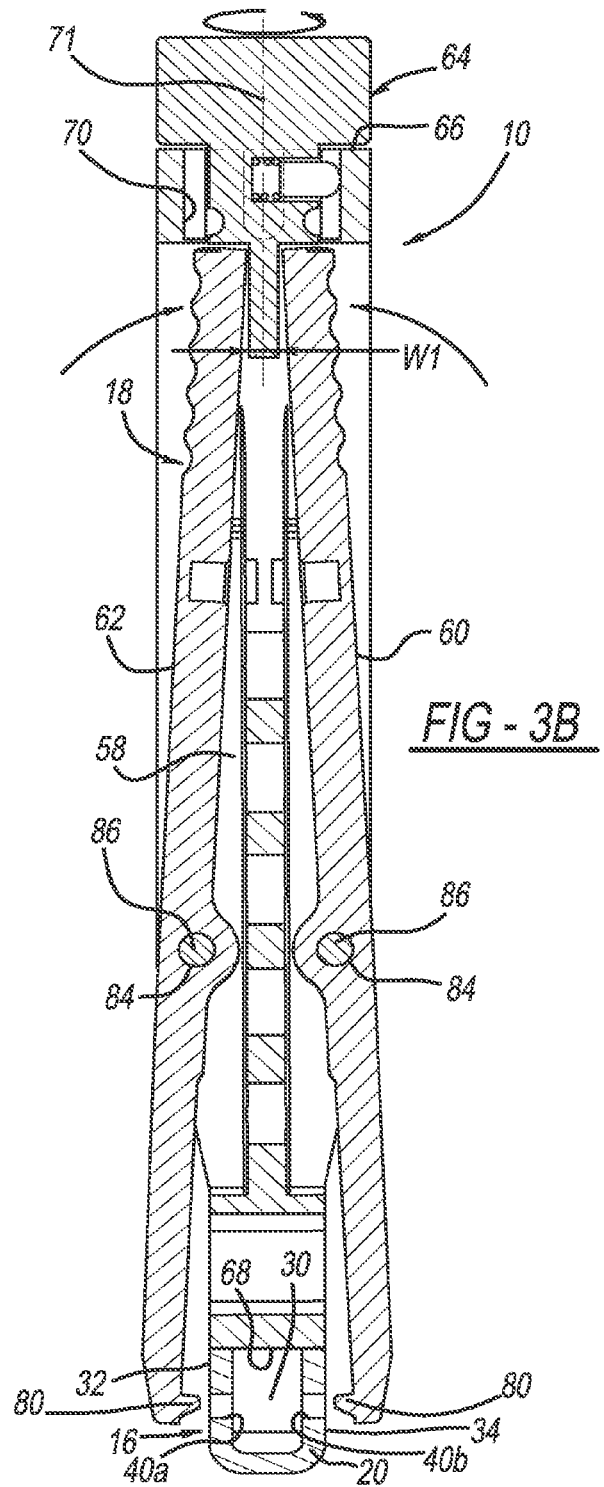

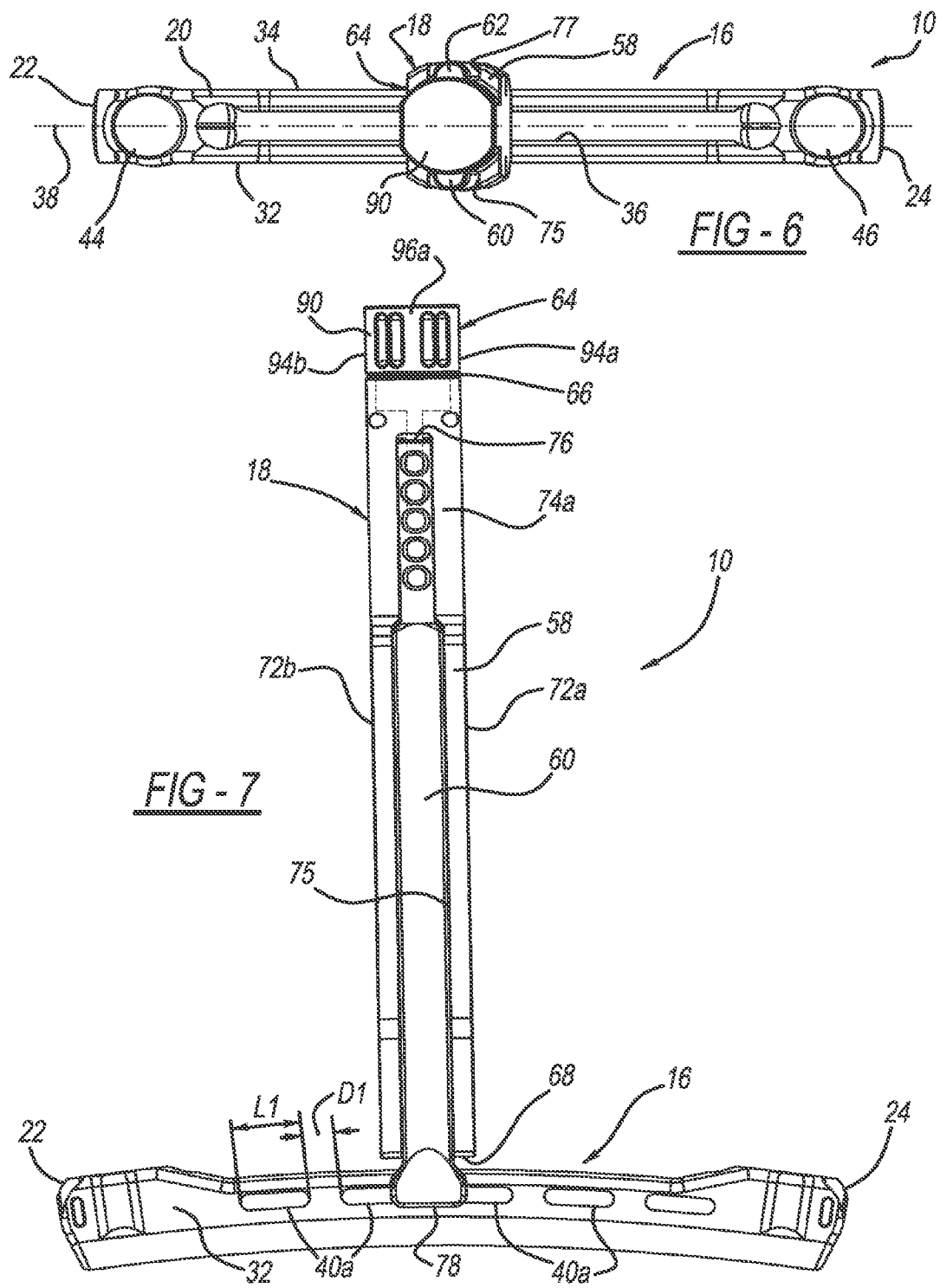

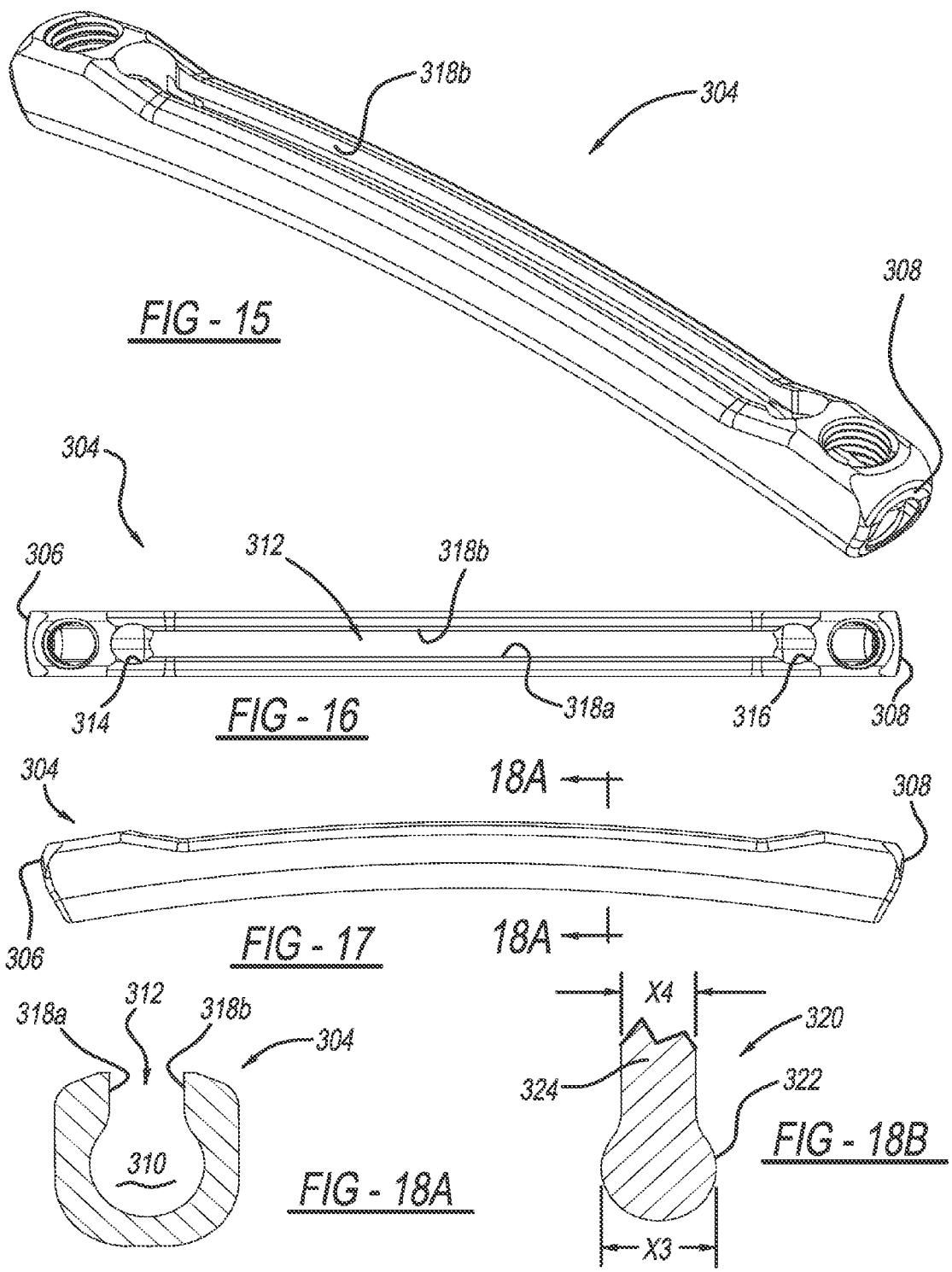

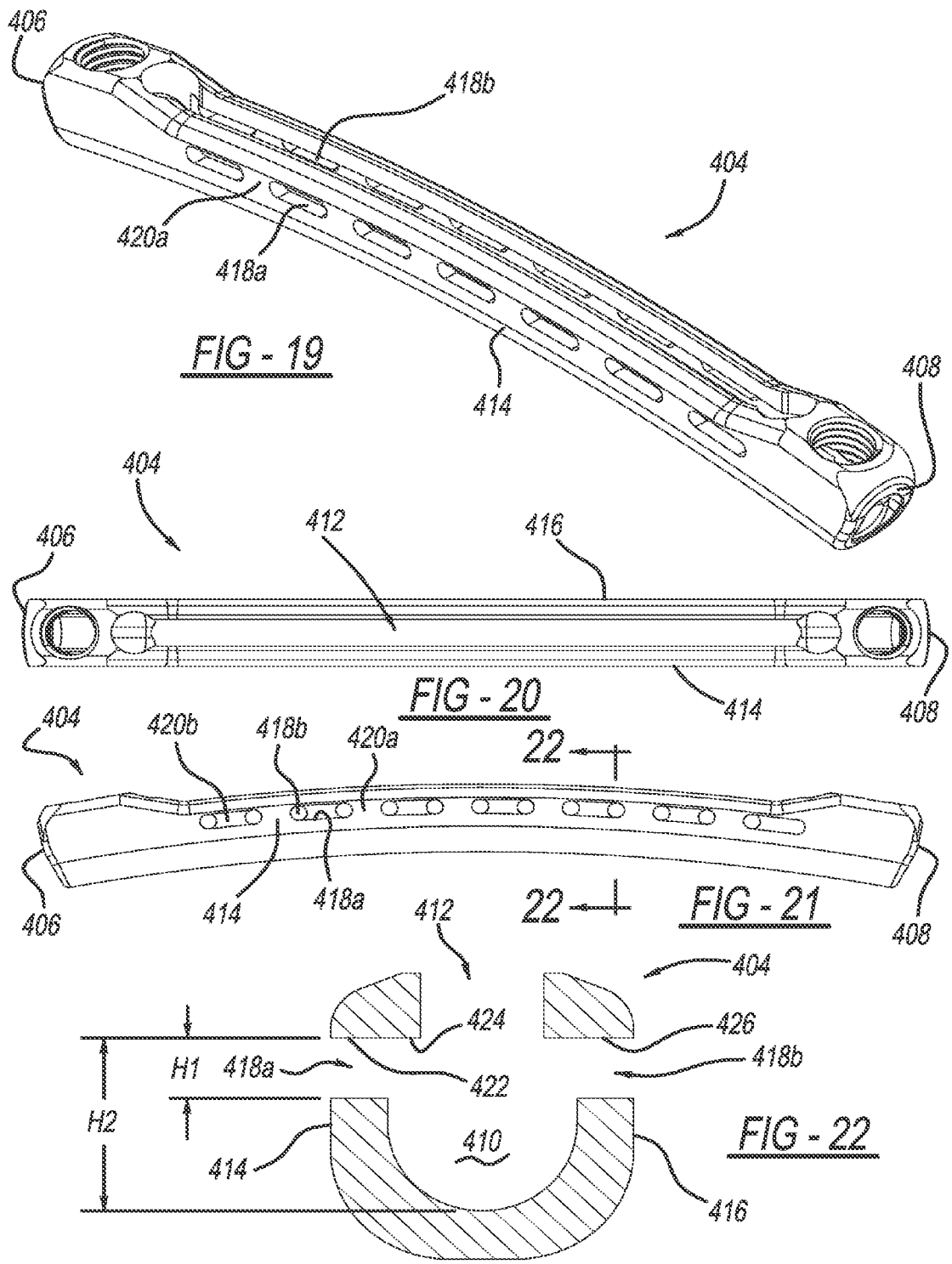

ANCHOR AND ROD CONNECTOR

FIELD

The present disclosure relates to a system and method for connecting and distracting surgical rods, and more particularly to a system and method for connecting and distracting at least two spinal rods in an end-to-end configuration.

BACKGROUND

This section provides background information related to the present disclosure and is not necessarily prior art.

Various surgical procedures may include the use of a rod to interconnect bones and/or various types of surgical implants. For example, a surgical procedure performed on a spine may require the use of a spinal rod to interconnect at least two vertebrae, or to connect a vertebra to a spinal implant. Some surgical procedures require the use of multiple rods. Various systems and methods have been developed for interconnecting multiple rods during a surgical procedure, including systems and methods for interconnecting multiple rods in an end-to-end or parallel configuration. While placing and interconnecting multiple rods in a connector during a surgical procedure, it may be desirable to adjust a distance between the rods and/or a distance between the connector and the rod. Additionally, it may be desirable to have a connector that can be coupled with curved rods, to adequately match patient anatomy.

While known spinal rod systems have proven to be acceptable for their intended purposes, a continuous need for improvement in the relevant arts remains.

SUMMARY

This section provides a general summary of the disclosure, and is not a comprehensive disclosure of its full scope or all of its features.

According to one particular aspect, the present disclosure provides a method of adjusting a distance between a first surgical rod and a second surgical rod. The method includes providing a surgical rod connector. The surgical rod connector includes a housing with first and second ends and a longitudinal passage extending between the first end and the second end. The method also includes positioning the first surgical rod in the first end of the housing and positioning the second surgical rod in the second end of the housing. The method further includes mounting an anchor mechanism to the connector and applying a force on the anchor mechanism and a corresponding force on one of the first and second surgical rods to distract the first and second surgical rods.

In some configurations, the anchor mechanism may include first and second arms for removably engaging the housing.

In some configurations, the first arm may include at least one first projection, the second arm may include at least one second projection, and the housing may include first and second slots. The at least one first projection may be removably received by the first slot and the at least one second projection may be removably received by the second slot In some configurations, the first and second slots may be arranged in a first plane, and the housing may include an opening in communication with the longitudinal passage. The opening may be arranged in a second plane substantially perpendicular to the first plane.

In some configurations, the anchor mechanism may further include an anchor housing. The first and second arms may be pivotably mounted to the anchor housing for rotation about a first axis and a second axis, respectively.

In some configurations, the anchor housing may include first and second receiving slots. The first and second arms may be pivotably received within the first and second receiving slots.

In some configurations, the housing may extend arcuately between the first and second ends.

In some configurations, the anchor mechanism may include an anchor housing and a locking mechanism rotatably mounted to the anchor housing. The locking mechanism may be operable to rotate about a first axis.

In some configurations, the anchor mechanism may further include a first arm pivotably mounted to the anchor housing for rotation about a second axis and a second arm pivotably mounted to the anchor housing for rotation about a third axis.

In some configurations, the first axis may be substantially perpendicular to the second and third axes.

In some configurations, the anchor housing may extend between a first end and a second end. The locking mechanism may extend from the first end of the anchor housing and the first and second arms may extend from the second end of the anchor housing.

In some configurations, the locking mechanism may include a first portion having a first peripheral surface and the housing may include a second peripheral surface similarly sized and shaped as the first peripheral surface.

In some configurations, the locking mechanism may include a second portion extending from the first portion. The second portion may be mounted within the housing.

In some configurations, the anchor mechanism may include a first actuating member, a second actuating member pivotably coupled to the first actuating member for rotation about a first axis, and a distracting member coupled to the second actuating member.

In some configurations, the first actuating member may include first and second arms for removably engaging the housing.

In some configurations, the first actuating member may further include first and second legs. The first and second arms may be pivotably mounted to the first and second legs, respectively, for rotation about a first axis and a second axis, respectively.

In some configurations, the distracting member extends between the first and second legs.

In some configurations, the anchor mechanism may further comprise an adjustment member rotatably coupled to the second actuating member. The distracting member may be threadably engaged with the adjustment member.

In some configurations, the adjustment member may be operable to adjust the position of the distracting member along a second axis that is perpendicular to the first axis.

In some configurations, the first actuating member may include first and second arms for removably engaging the housing. The first and second arms may be pivotably mounted to the anchor housing for rotation about a third axis and a fourth axis, respectively. The third and fourth axes may extend in a direction perpendicular to the first axis and to the second axis.

In some configurations, the connector may include a central passage, a first slot extending through the connector in a first direction, and a second slot extending through the connector in a second direction perpendicular to the first direction. The first and second slots may be communication with the central passage.

In some configurations, the central passage may be at least partially defined by a first upper surface, and the second slot may be at least partially defined by a second upper surface that is aligned with the first upper surface.

In some configurations, the connector may further include a third slot extending through the connector in second direction. The third slot may oppose the second slot and may be at least partially defined by a third upper surface that is aligned with the first upper surface.

In some configurations, the connector may include a central passage and a first slot extending through the connector and in communication with the central passage. The central passage may be at least partially defined by a concave sidewall. The first slot may be at least partially defined by opposed planar sidewalls.

In some configurations, the connector may include a central passage, a first slot extending through the connector in a first direction, and a second slot extending through the connector in a second direction perpendicular to the first direction. The first and second slots may be in communication with the central passage.

According to another particular aspect, the present disclosure provides a device for distracting first and second surgical rods. The device includes a connector and an anchor mechanism. The connector includes a housing with a first end, a second end, and a longitudinal passage extending therebetween. The first and second ends of the housing receive the first and second surgical rods, respectively. The anchor mechanism is removably securable to the housing for opposing a force to distract the first and second surgical rods.

According to yet another particular aspect, the present disclosure provides a method of adjusting a distance between a first surgical rod and a second surgical rod. The method may include providing a surgical rod connector having a housing with first and second ends and a longitudinal passage extending between the first end and the second end. The method may also include positioning the first surgical rod in the first end and positioning the second surgical rod in the second end. The method may further include mounting an anchor mechanism to the connector. The method can also include applying a force on the anchor mechanism and a corresponding force on one of the first and second surgical rods to distract the first and second surgical rods relative to one another.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3A is a cross-sectional view taken along the line 3A-3A of FIG. 1, an anchor of the system shown in a locked position.

FIG. 3B is a cross-sectional view similar to FIG. 3A, the anchor of the system shown in an unlocked position.

FIG. 6 is a top view of the connector and the anchor of the system of FIG. 1.

FIG. 7 is a side view of the connector and the anchor of the system of FIG. 1.

FIG. 15 is a perspective view of another connector of the system of FIG. 8.

FIG. 16 is a top view of the connector of FIG. 15.

FIG. 17 is a side view of the connector of FIG. 15.

FIG. 18A is a cross-sectional view taken along the line 18A-18A of FIG. 17.

FIG. 18B is a cross-sectional view of a cutting tool for use in manufacturing the connector of FIG. 15.

FIG. 19 is a perspective view of another connector of the system of FIG. 8.

FIG. 20 is a top view of the connector of FIG. 19.

FIG. 21 is a side view of the connector of FIG. 19.

FIG. 22 is a cross-sectional view taken along the line 22-22 of FIG. 21.

Corresponding reference numerals indicate corresponding parts throughout the several views of the drawings.

DETAILED DESCRIPTION

Figure 1:
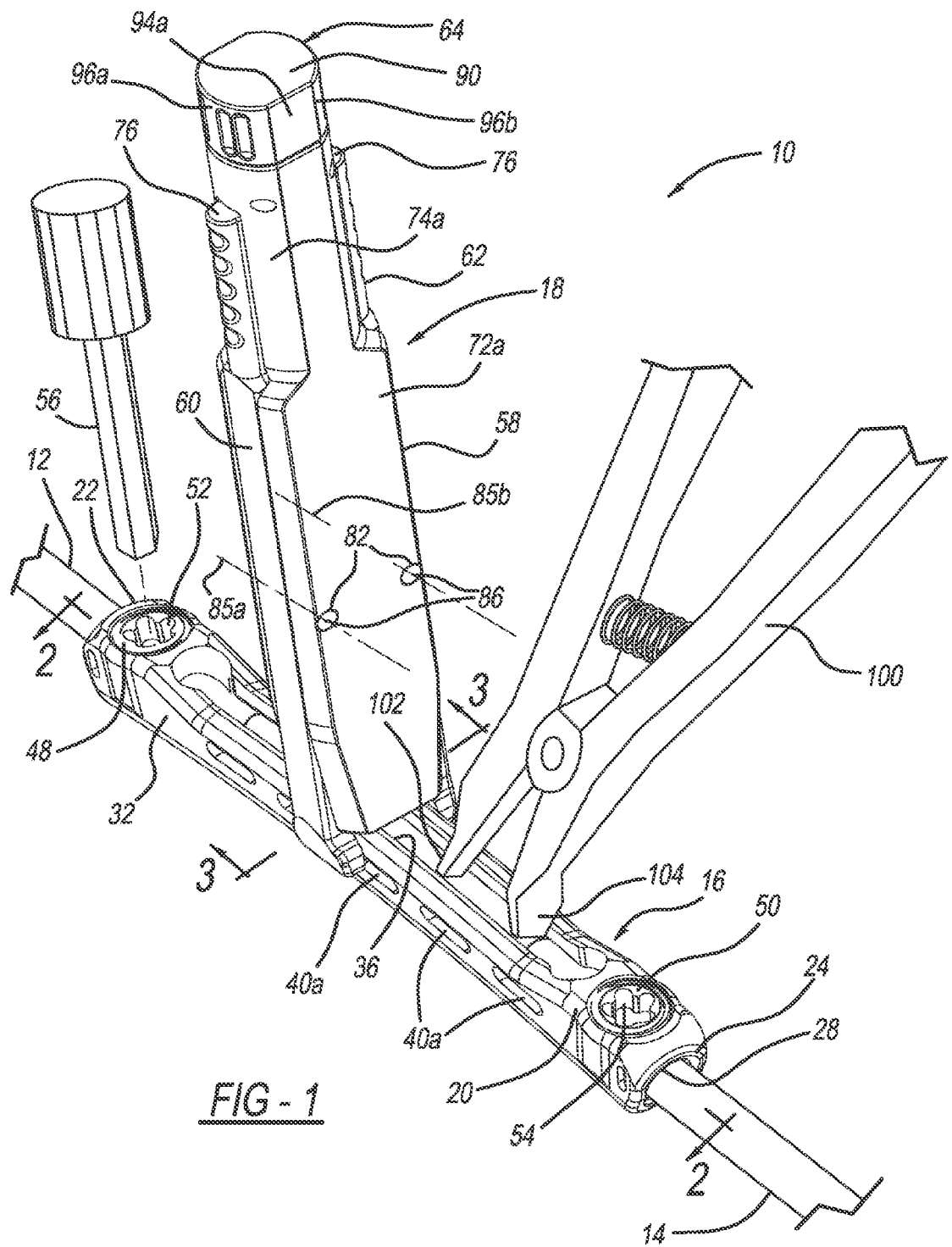
FIG. 1 is a perspective view of a system for connecting and distracting a surgical rod, in accordance with the principles of the present disclosure.

Example embodiments will now be described more fully with reference to the accompanying drawings.

With general reference to the drawings, a system for connecting and distracting at least one surgical rod in accordance with the present teachings is illustrated and identified at reference character 10. According to one exemplary use, the system 10 may be used to connect and distract a first rod 12 relative to a second rod 14. The system 10, including the first and second rods 12, 14, may be used to repair a bone (not shown) or secure a bone relative to an implant (not shown) during a surgical procedure. By way of example only, the first and second rods 12, 14 may be spinal rods. Accordingly, the system 10 may be used to secure, or otherwise correct or repair, a spine. It will be appreciated, however, that the principles of the present disclosure may be adapted to secure, or otherwise repair, various bones and various implants.

Figure 2:
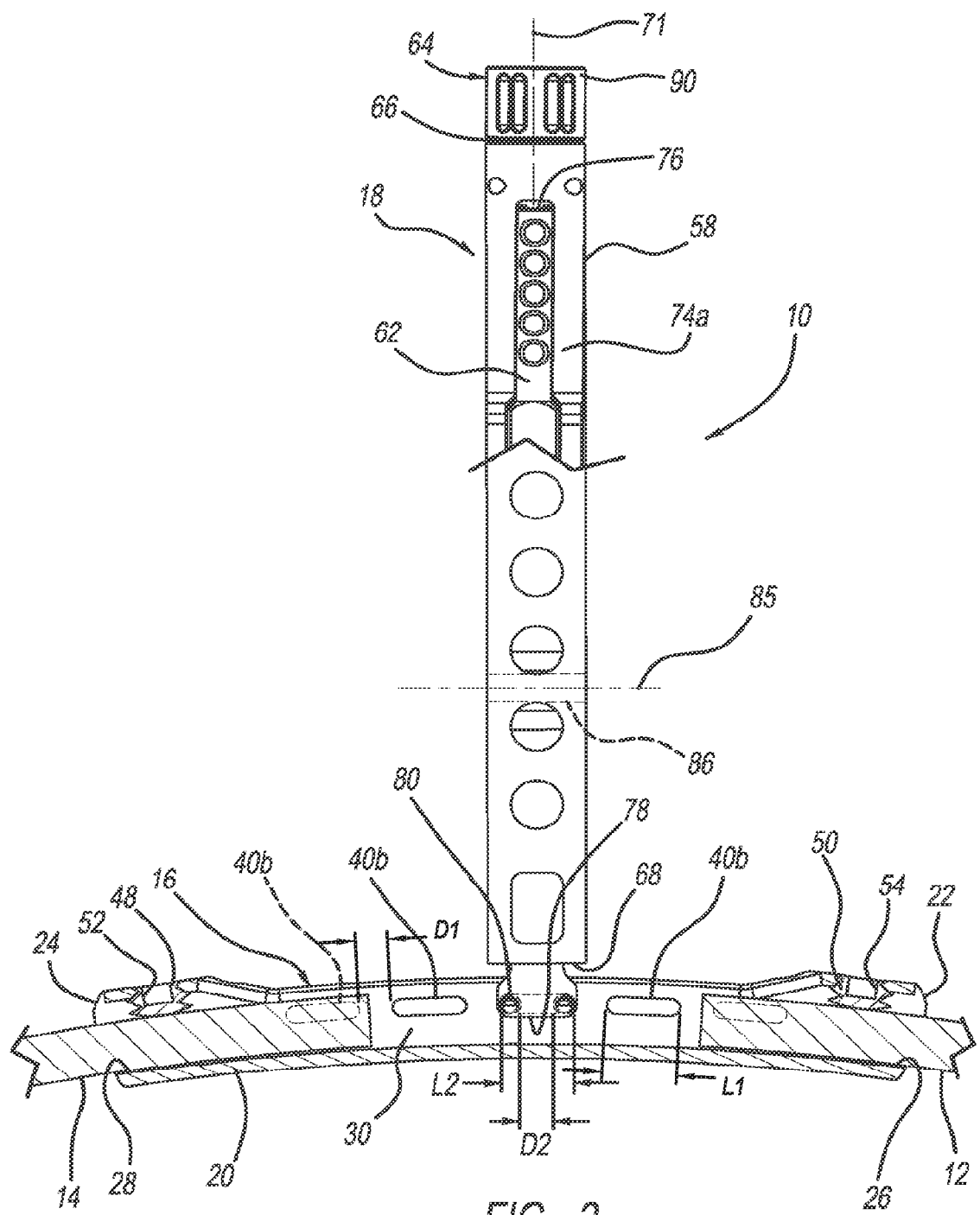
FIG. 2 is a side view of the system of FIG. 1 shown partially in section.

The system 10 may generally include a connector 16 and an anchor 18. The connector 16 may include a housing or body 20 for connecting the first and second rods 12, 14 in a substantially parallel configuration (e.g., end-to-end alignment). The body 20 may extend longitudinally between a first end 22 and a second end 24. As illustrated in FIG. 2, in one configuration the body 20 may extend arcuately between the first and second ends 22, 24. The first end 22 may include a first rod opening 26 formed therein for receiving the first rod 12 and the second end 24 may include a second rod opening 28 formed therein for receiving the second rod 14. A channel or passage 30, in which a portion of the first rod 12 and a portion of the second rod 14 may be positioned, may extend between the first rod opening 26 and the second rod opening 28. It will be appreciated that a radius of curvature of the arcuately extending body 20, including the passage 30, may be substantially equal to a radius of curvature of the curved or arcuately extending rods 12, 14, as illustrated in FIG. 2.

In one configuration, the passage 30, including the first and second rod openings 26, 28, may be substantially cylindrical in shape, including a generally circular cross section. In other configurations, the passage 30 may have different shapes. For example, the passage 30, including the first and second rod openings 26, 28, may have a polygonal, square, elliptical, rectilinear, or other suitable cross-sectional shape. In this regard, it will be appreciated that the cross-sectional shape of the passage 30, including the first and second rod openings 26, 28, may approximately correspond to the cross-sectional shape of the first and/or second rod 12, 14 received thereby. In certain configurations, the first rod opening 26, the second rod opening 28, and portions of the passage 30 therebetween may be distinct in size and shape to receive and connect two rods of different size and/or shape. Explaining further, it will be understood that the rods 12, 14 may have any cross-sectional shape within the scope of the present teachings provided that the rods 12, 14 cooperate with the connector 16. In addition, as illustrated in at least FIG. 2, the rods 12, 14 may have a generally arcuate or curved profile extending along the length thereof.

Figure 5:
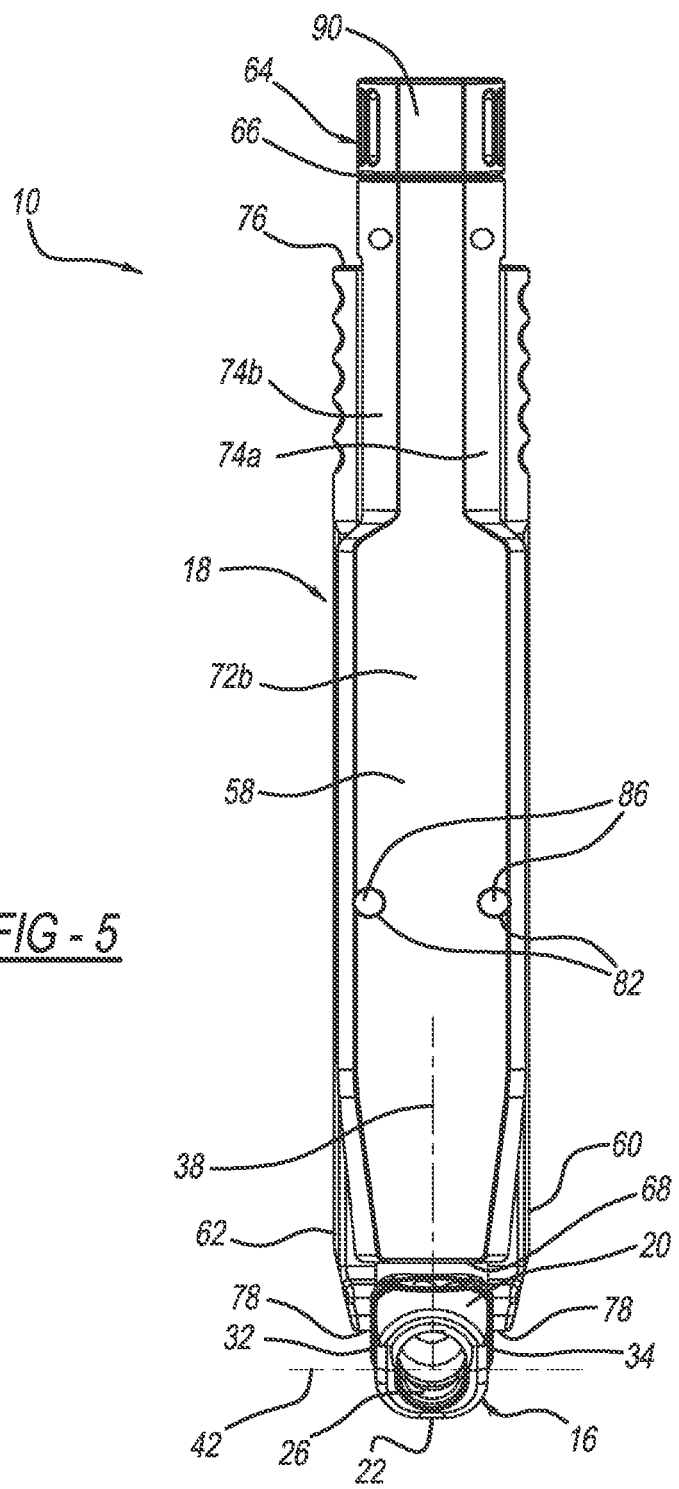
FIG. 5 is an end view of a connector and the anchor of the system of FIG. 1.
Figure 8:
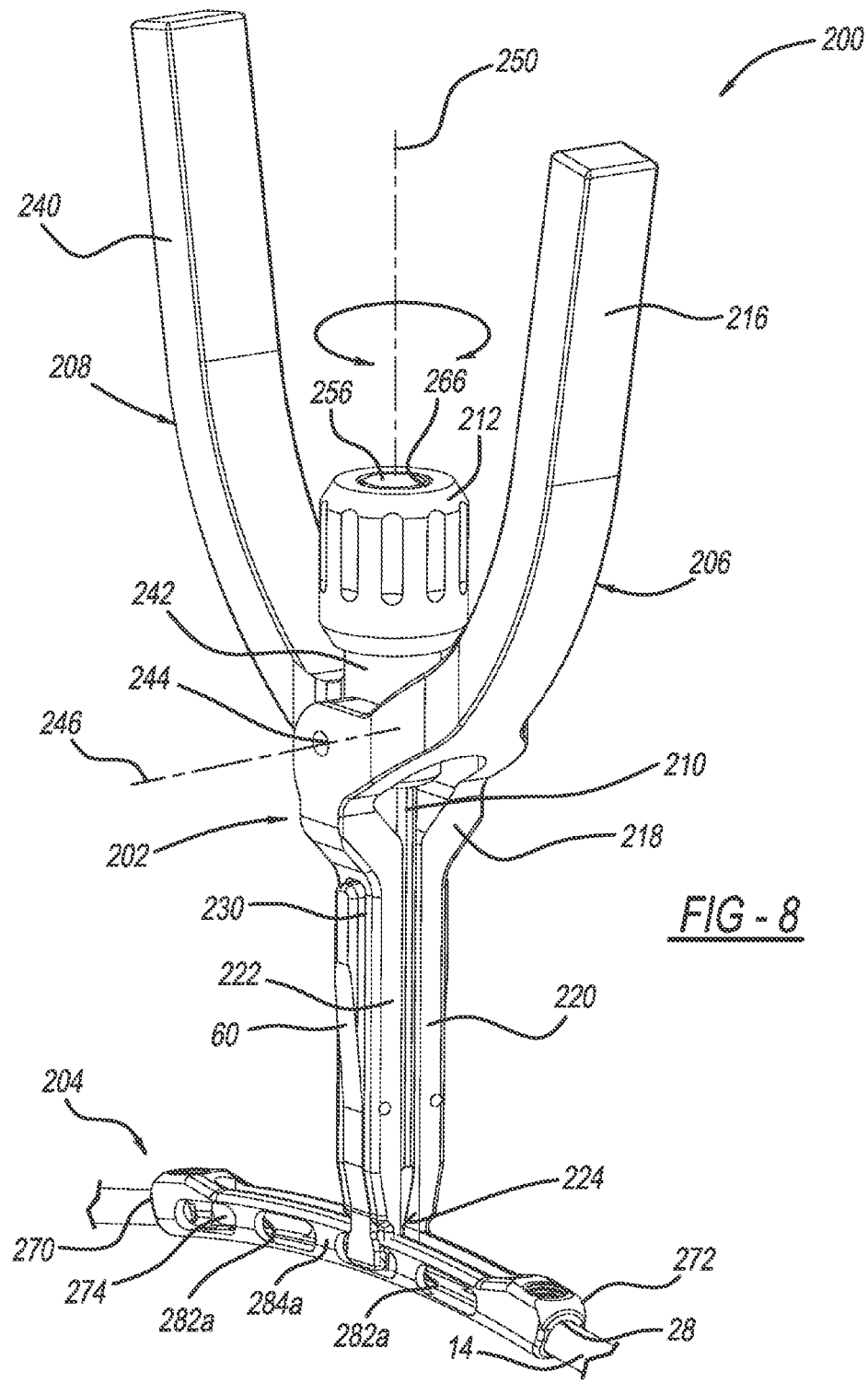
FIG. 8 is a perspective view of another configuration of a system for connecting and distracting a surgical rod, in accordance with the principles of the present disclosure.

The body 20 of the connector 16 may also include first and second sidewalls 32, 34 and an elongated opening or slot 36. The first and second sidewalls 32, 34 may extend between the first and second ends 22, 24. The elongated slot 36 may extend longitudinally between the first and second sidewalls 32, 34 and open into and communicate with the passage 30. The elongated slot 36 may be symmetrically oriented in a first plane 38 (FIGS. 3A and 5). In this regard, the elongated slot 36 may be oriented to allow access to the passage 30 from the top of the connector 16, relative to the view in FIG. 3A. In one configuration, the first sidewall 32 is substantially parallel to the second sidewall 34 and to the first plane 38. In other configurations, the first and second sidewalls 32, 34 may be disposed in an arcuate configuration or at other angles relative to each other.

The first and second sidewalls 32, 34 may further include a plurality of spaced apart slots 40a, 40b, respectively, oriented along the length of the body 20 between the first end 22 and the second end 24. The slots 40a, 40b may open into and communicate with the passage 30. In one configuration, the first sidewall 32 includes five slots 40a and the second sidewall 34 includes five slots 40b. It will be appreciated, however, that the first and second sidewalls 32, 34 may include greater or less than five slots 40a, 40b within the scope of the present disclosure. In some configurations, the slots 40a in the first sidewall 32 may be substantially aligned with, and of a similar size and shape as, the slots 40b in the second sidewall 34. It will also be appreciated, however, that the slots 40a may be offset from, or otherwise staggered relative to, the slots 40b. In this regard, as illustrated in FIG. 7, the slots 40a, 40b may have a longitudinally extending length L1, and consecutive slots 40a, 40b may be separated by a longitudinally extending distance D1.

With reference to FIGS. 3A, 5 and 7, at least a portion of each of the slots 40a, 40b may be symmetrically oriented in and about an arc 42. The arc 42 and the first plane 38 may define an angle α therebetween. In one configuration, the angle α may be substantially equal to ninety degrees. It will be appreciated, however, that the angle α may be greater or less than ninety degrees within the scope of the present disclosure. While the slots 40a, 40b are described and illustrated herein as being oriented in and about the arc 42, it will also be appreciated that the slots 40a may be oriented in the arc 42 and the slots 40b may be oriented in another arc (not shown).

Figure 4:
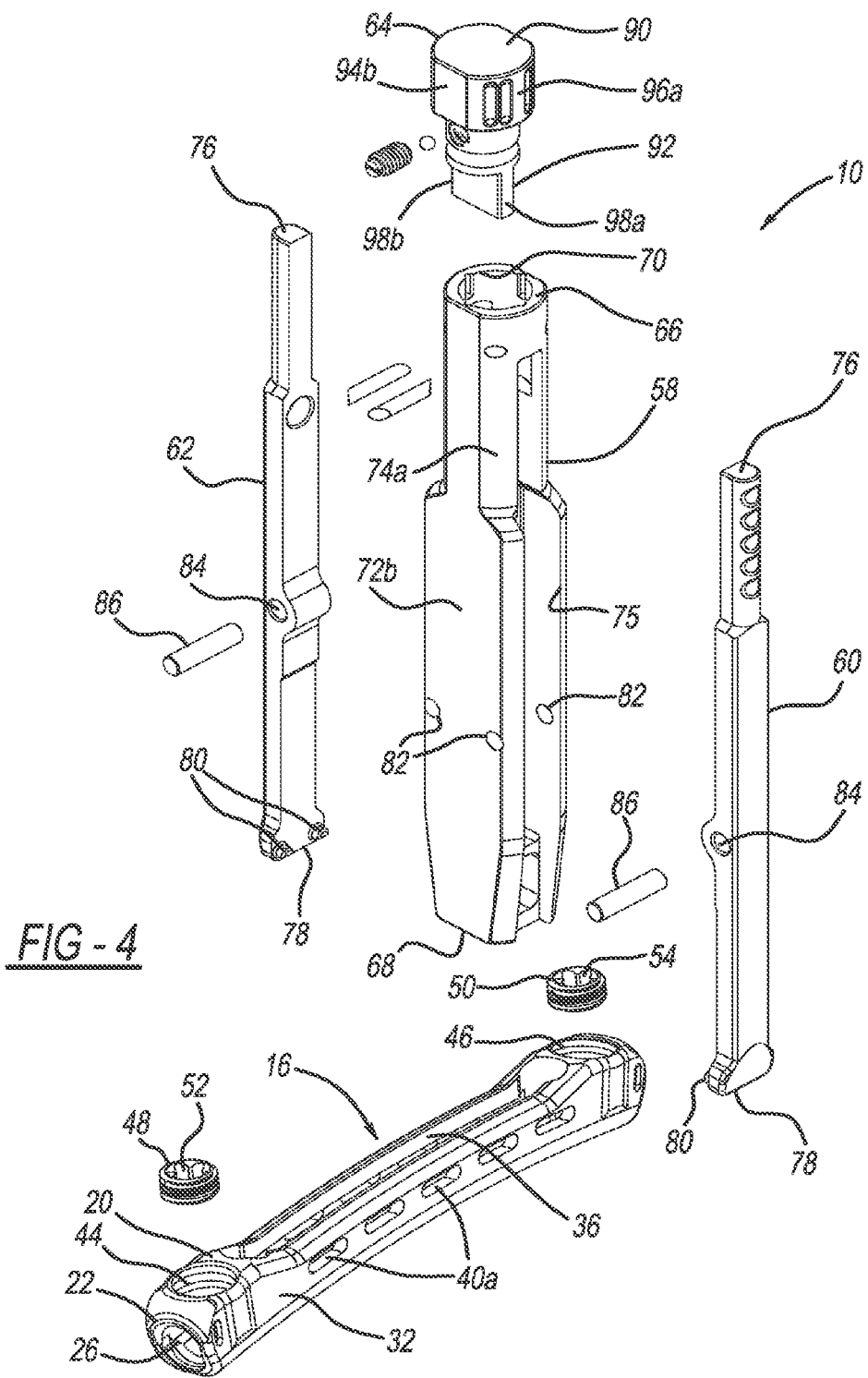
FIG. 4 is an exploded view of the system of FIG. 1.

As illustrated in FIGS. 4 and 6, the body 20 of the connector 16 may further include first and second apertures 44, 46 for receiving first and second fasteners or closure mechanisms 48, 50, respectively. The first and second apertures 44, 46 may communicate with the passage 30. In one configuration, the first aperture 44 is positioned proximate the first end 22 of the body 20 and the second aperture 46 is positioned proximate the second end 24 of the body 20. As illustrated in FIG. 6, the first and second apertures 44, 46 may be symmetrically oriented in the first plane 38.

The first closure mechanism 48 may threadably mount within the first aperture 44 for locking the position of the first spinal rod 12 within the passage 30. The second closure mechanism 50 may threadably mount within the second aperture 46 for locking the position of the second spinal rod 12 within the passage 30. In one configuration, the first and second closure mechanisms 48, 50 are threaded set screws. In this regard, the first and second closure mechanisms 48, 50 may each include a driver-receiving portion 52, 54, respectively, such as a hexagonal or multi-lobular bore, for operatively receiving a driver 56 (FIG. 1), such as a hexagonal or multi-lobular key. The first and second closure mechanisms 48, 50 may be mounted within the first and second apertures 44, 46 using the driver 56.

The anchor 18 may include a body or housing 58, a first arm 60, a second arm 62, and a locking mechanism 64. The first and second arms 60, 62 may be coupled to the housing 58 and may be operable to selectively engage the body 20 of the connector 16 in a first configuration (FIG. 3A). The locking mechanism 64 may be coupled to the housing 58 and may be operable to selectively lock or secure the first and second arms 60, 62 in the first configuration (FIG. 3a).

The housing 58 may extend longitudinally between a first end 66 and a second end 68. The first end 66 may include a longitudinally extending opening 70 (FIG. 4) formed therein. As illustrated in FIG. 3A, the opening 70 may define a longitudinal axis 71. The housing 58 may further include first and second sidewalls 72a, 72b and third and fourth sidewalls 74a, 74b. The first and second sidewalls 72a, 72b may include a substantially planar profile. The third and fourth sidewalls 74a, 74b may include a substantially arcuate profile and may include first and second arm receiving slots 75, 77. The first and second arm receiving slots 75, 77 may extend longitudinally from the second end 68 of the housing 58. The first arm receiving slot 75 may face, or generally oppose, the second arm receiving slot 77.

The first arm 60 may be substantially similar to the second arm 62. In this regard, the first and second arms 60, 62 may extend longitudinally between a first end 76 and a second end 78. The second end 78 of the first and second arms 60, 62 may include at least one detent or projection 80. As illustrated in FIG. 2, in one configuration, the second end 78 of the first and second arms 60, 62 includes two projections 80 defining a length L2 and defining a distance D2 between the projections 80. The length L2 may be substantially equal to, or slightly less than, the length L1 of the slots 40a, 40b. The distance D2 may be substantially equal to, or slightly greater than, the distance D1 between consecutive slots 40a, 40b.

In an assembled configuration, the first arm 60 may be pivotably mounted in the first arm receiving slot 75, and the second arm 62 may be pivotably mounted in the second arm receiving slot 77, such that the second end 78 of the first and second arms 60, 62 extends from and beyond the second end 68 of the housing 58. In this regard, as illustrated in FIG. 4, the housing 58 may include at least one bore 82, and the first and second arms 60, 62 may include at least one bore 84. In the assembled configuration, the bore 82 and the bore 84 may define first and second axes 85a, 85b that are substantially perpendicular to the axis 71. A pin 86 may be mounted in the bore 82 and in the bore 84, such that the first and second arms 60, 62 can pivot about the axes 85a, 85b, respectively.

With reference to FIG. 4, the locking mechanism 64 may include a first portion 90 and a second portion 92. A peripheral surface of the first portion 90 may be similarly sized and shaped as a peripheral surface of the housing 58. In this regard, the first portion 90 may include first and second sidewalls 94a, 94b and third and fourth sidewalls 96a, 96b. The first and second sidewalls 94a, 94b may include a substantially planar profile. The third and fourth sidewalls 96a, 96b may include a substantially arcuate profile. The second portion 92 of the locking mechanism 64 may include first and second stopping ends 98a, 98b. The first and second stopping ends 98a, 98b may include a width W1 and define a distance D3 therebetween. The width W1 may be less than the distance D3.

In an assembled configuration, the first portion 90 of the locking mechanism 64 may extend from the first end 66 of the housing 58. The second portion 92 of the locking mechanism 64 may be rotatably mounted in the opening 70 of the housing 58, such that the locking mechanism 64 can rotate about the axis 71 between a locked position (FIG. 3A) and an unlocked position (FIG. 3B). In the locked position, the first and second stopping ends 98a, 98b may face, or otherwise abut, the first and second arms 60, 62, to prevent the first and second arms 60, 62 from pivoting about the axes 85a, 85b, respectively. In the unlocked position, the first and second stopping ends 98a, 98b may be offset from the first and second arms 60, 62, to allow the first and second arms 60, 62 to pivot about the axes 85a, 85b, respectively. It will also be appreciated that in the locked position, the substantially planar first and second sidewalls 94a, 94b of the locking mechanism 64 may be aligned with the substantially planar first and second sidewalls 72a, 72b of the housing 58. In the unlocked position, the substantially planar first and second sidewalls 94a, 94b may be aligned with the arcuate third and fourth sidewalls 74a, 74b of the housing 58. In this way, the alignment of the first and second sidewalls 94a, 94b relative to the first and second sidewalls 72a, 72b or the third and fourth sidewalls 74a, 74b of the housing 58 can indicate whether the locking mechanism 64 is in the locked position or the unlocked position.

In operation, the first and second rods 12, 14 can be extended into the passage 30 of the connector 16 through the first and second rod openings 26, 28, respectively. The first and second arms 60, 62 can be rotated about the axes 85a, 85b, respectively, to increase a distance between the second ends 78 of the first and second arms 60, 62, and the projections 80 can be positioned in the slots 40a, 40b. The locking mechanism 64 can be rotated about the axis 71 such that the first and second stopping ends 98a, 98b face, or otherwise abut, the first and second arms 60, 62, thus locking the anchor 18 to the connector 16 by preventing the first and second arms 60, 62 from pivoting about the axes 85a, 85b, respectively.

A distractor 100, including first and second jaws or ends 102, 104, may be positioned within the slot 36 and the passage 30 of the connector body 20. Insofar as the present teachings are concerned, it will be understood that the distractor 100 is conventional in both construction and operation. The first end 102 of the distractor may be positioned adjacent the housing 58 of the anchor 18. The second end 104 of the distractor 100 may be positioned adjacent the second rod 14. The distance between the first and second ends 102, 104 of the distractor 100 may be increased to apply a force F1 on the anchor 18 and a corresponding force F2 on the second rod 14. As illustrated, the force F1 and the corresponding force F2 are applied directly to the anchor 18 and the second rod 14, respectively. Applying the force F1 on the anchor 18 and the force F2 on the second rod 14 may increase the distance between the second rod 14 and the anchor 18. When a desired distance between the second rod 14 and the anchor 18 is achieved, the closure mechanism 50 may be tightened within the aperture 44 using the driver 56, such that the closure mechanism 50 engages the second rod 14 and secures the second rod 14 within the passage 30.

It will be appreciated that the distractor 100 and anchor 18 may also be used to achieve a desired distance between the first rod 12 and the anchor 18, in the same manner described above. When a desired distance between the first and/or second rods 12, 14 and the anchor 18 is realized, the locking mechanism 64 can be rotated about the axis 71 such that the first and second stopping ends 98a, 98b are offset from the first and second arms 60, 62, thus allowing the first and second arms 60, 62 to pivot about the axes 85a, 85b, respectively. The first and second arms 60, 62 may then be pivoted about the axes 85a, 85b, respectively, to remove the projections 80 from the slots 40a, 40b, and to remove the anchor 18 from the connector 16.

With reference to FIGS. 8 through 10B, another system for connecting and distracting at least one surgical rod in accordance with the present teachings is illustrated and identified at reference character 200. The structure and function of the system 200 may be substantially similar to that of the system 10 illustrated in FIGS. 1 through 7, apart from any exceptions described below and/or shown in the Figures. Therefore, the structure and/or function of similar features will not be described again in detail, and like reference numerals may be used to describe like features and components.

The system 200 may include an anchor 202 and a connector 204. While the anchor 202 is illustrated and described herein as being operable with the connector 204, it will be appreciated that the anchor 202 may also be operable with any of the connectors described herein, including the connector 16. The anchor 202 may include a first actuating member 206, a second actuating member 208, the first arm 60, the second arm 62, a distracting member 210, and an adjustment member 212. As will be explained in more detail below, the anchor 202 may be operable to engage and secure the connector 204 and also distract the first and/or second rod 12, 14 relative to the connector 204.

The first actuating member 206 may include a handle portion 216 and an engagement portion 218. As illustrated, the handle portion 216 may arcuately extend from the engagement portion 218. In this regard, the handle portion 216 may be integrally and monolithically formed with the engagement portion 218. It will be appreciated, however, that the handle portion 216 may also be separately formed and coupled to the engagement portion 218. The engagement portion 218 may include first and second legs 220, 222. The first and second legs 220, 222 may define a central channel or passage 224 therebetween. The first leg 220 may include a first channel or groove 230 extending longitudinally therein. The second leg 222 may include a second channel or groove (not shown) extending longitudinally therein. In this regard, the first groove 230 and the second groove may extend in a direction substantially parallel to the central passage 224.

Figure 9:
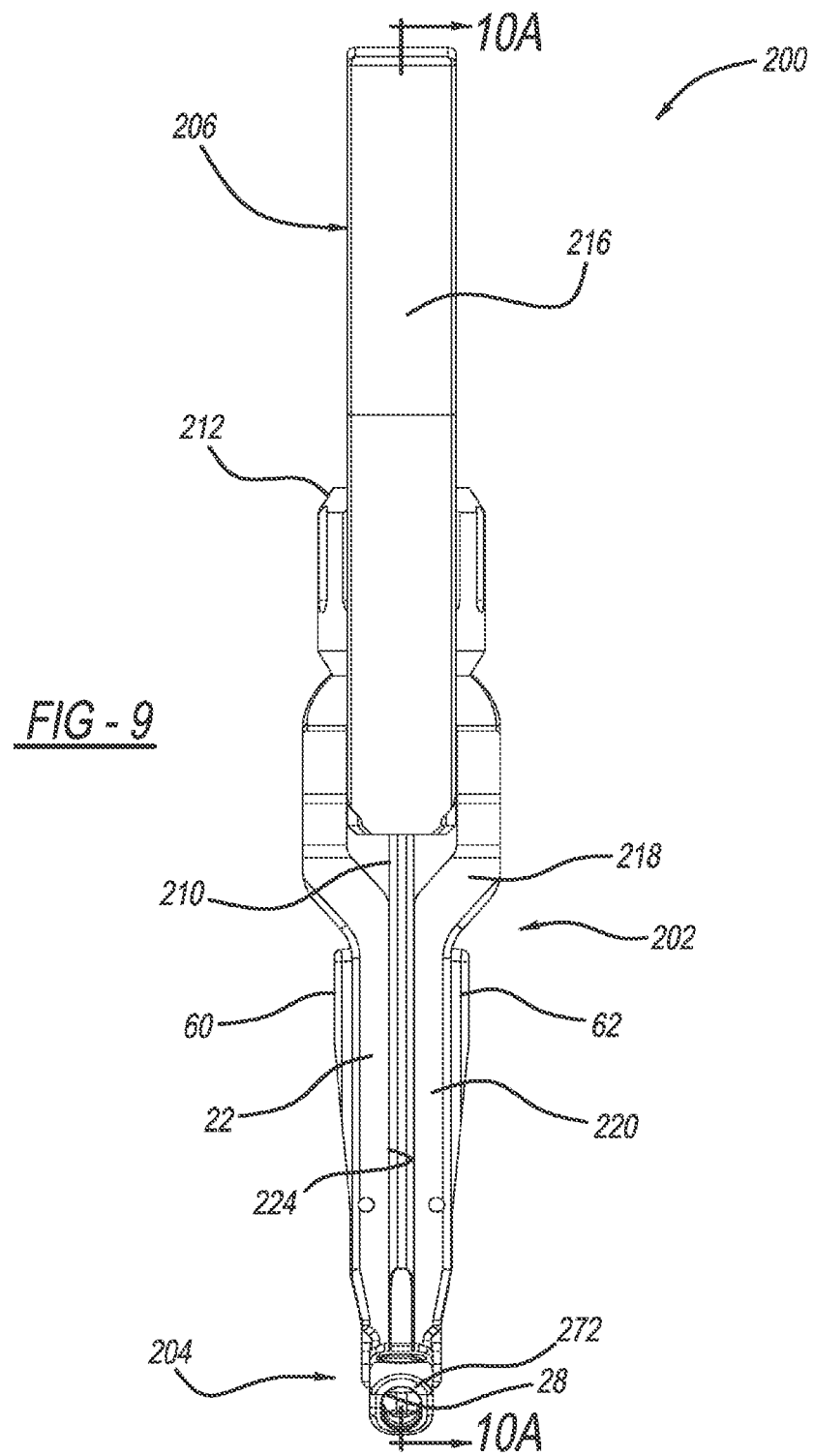
FIG. 9 is an end view of the system of FIG. 8.

As illustrated in FIG. 9, the first and second arms 60, 62 may be pivotably coupled to the first actuating member 206 and may be operable to selectively engage the connector 204 in a first configuration. The first arm 60 may be disposed in the first groove 230, and the second arm 62 may be disposed in the second groove. A biasing member (not shown) may be disposed between the first arm 60 and the first leg 220. Similarly, another biasing member (not shown) may be disposed between the second arm 62 and the second leg 222. The biasing members may bias the projections 80 into engagement with the connector 204 in the first configuration (FIG. 10A).

The second actuating member 208 may include a handle portion 240 and a distracting member receiving portion 242, and may be pivotably coupled to the first actuating member 206 for rotation about a hinge 244. The hinge 244 defines an axis of rotation 246. The handle portion 240 of the second actuating member 208 may be substantially similar to the handle portion 216 of the first actuating member 206. As illustrated, the handle portion 240 may extend arcuately from the distracting member receiving portion 242. In this regard, the handle portion 240 may be integrally and monolithically formed with the distracting member receiving portion 242. It will be appreciated, however, that the handle portion 240 may also be separately formed and coupled to the distracting member receiving portion 242.

Figure 10A:
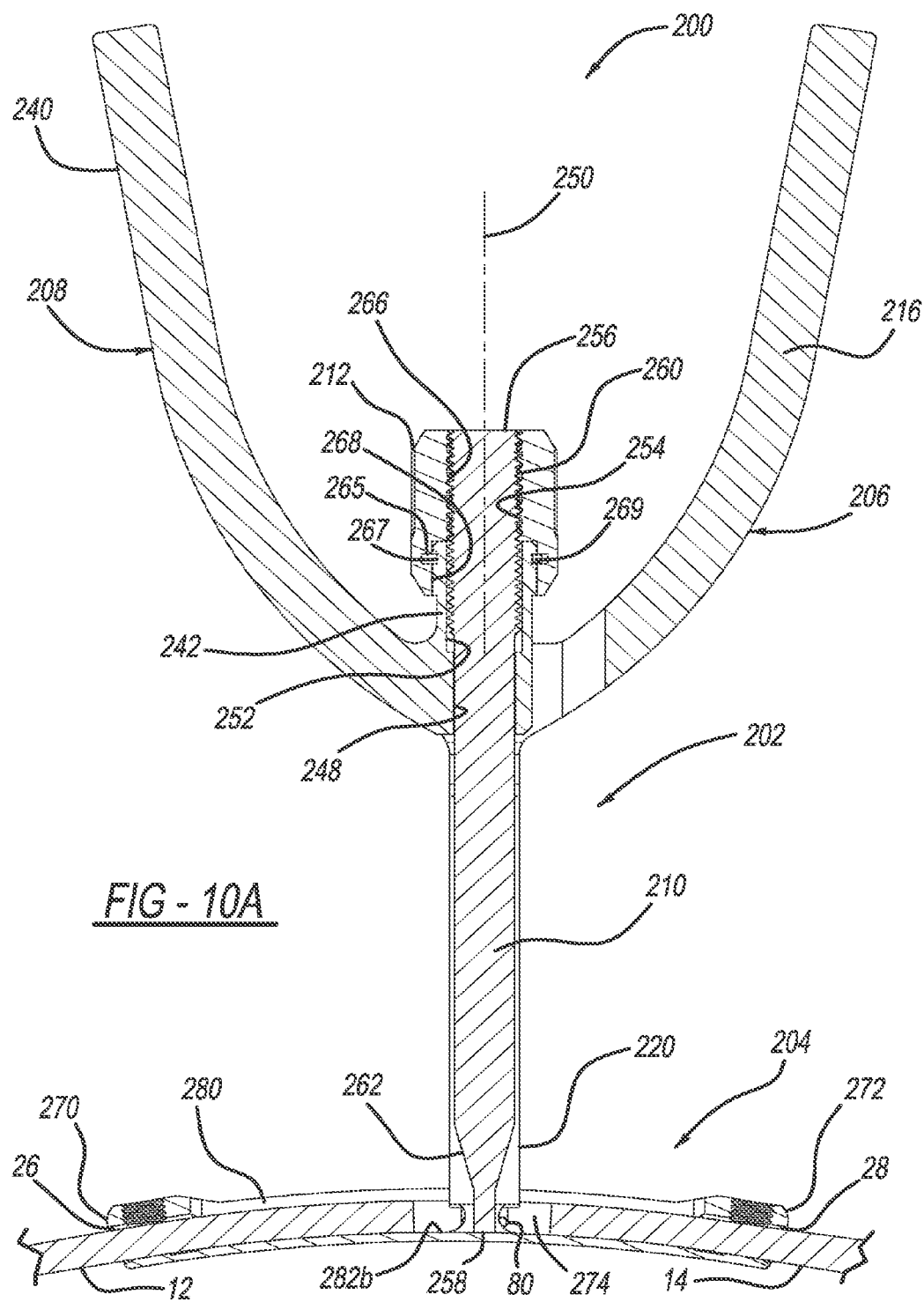
FIG. 10A is a cross-sectional view taken along the line 10A-10A of FIG. 9, the system shown in a first position.

As illustrated in FIG. 10A, the distracting member receiving portion 242 may define an aperture 248 therethrough. In an assembled configuration, the aperture 248 may open into the central passage 224 of the first actuating member 206. The aperture 248 may extend along an axis 250 that is substantially perpendicular to the axis of rotation 246, and may further define a counterbore 252.

The distracting member 210 may extend between a proximal end 256 and a distal end 258. The proximal end 256 may include a threaded portion 260. The distracting member 210 may include a tapered portion 262, such that the distal end 258 defines a reduced width portion of the distracting member 210. As illustrated in FIGS. 9 and 10A, in an assembled configuration, the distracting member 210 may be disposed within the central passage 224 of the first actuating member 206 and within the aperture 248 of the second actuating member 208.

With further reference to FIG. 10A, the adjustment member 212 may define an aperture 266 therethrough. The aperture 266 may include a threaded portion 254 and a counterbore portion 268. In an assembled configuration, the distracting member receiving portion 242 of the second actuating member 208 may be disposed within the counterbore portion 268, such that the aperture 266 opens into the aperture 248. The proximal end 256 of the distracting member 210 may be disposed within the aperture 266 of the adjustment member 212. As will be explained in more detail below, the adjustment member 212 may serve as a knob, allowing the user to rotate the adjustment member 212 about the axis 250, such that the threaded portion 254 engages the threaded portion 260 of the distracting member 210. In this regard, the adjustment member 212 may include a first annular groove 265 and the distracting member receiving portion 242 may include a second annular groove 267. In an assembled configuration, the first annular groove 265 may be aligned with the second annular groove 267. An O-ring, C-clip, or other similar retaining device 269 may be disposed within the first and second annular groove 265, 267, such that the adjustment member 212 can rotate relative to the distracting member receiving portion 242 about the axis 250. As such, threadably engaging the threaded portion 254 of the adjustment member 212 with the threaded portion 260 of the distracting member 210 can allow the distracting member 210 to move along, and parallel to, the axis 250

Figure 13:
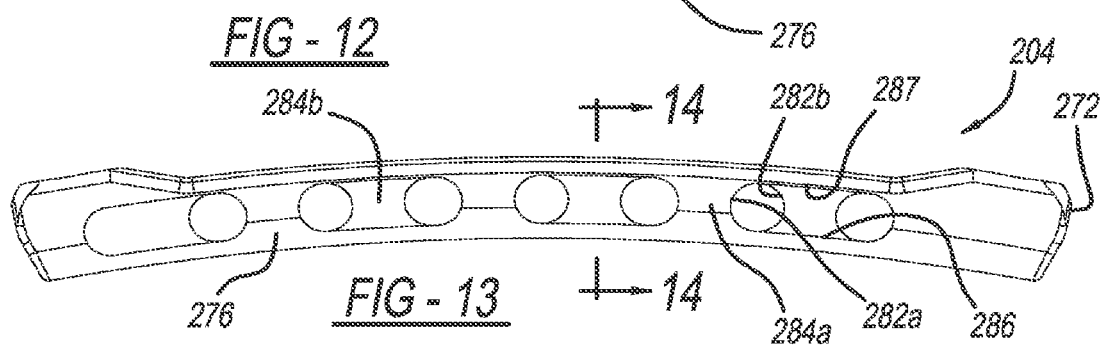
FIG. 13 is a side view of the connector of FIG. 1.
Figure 14:
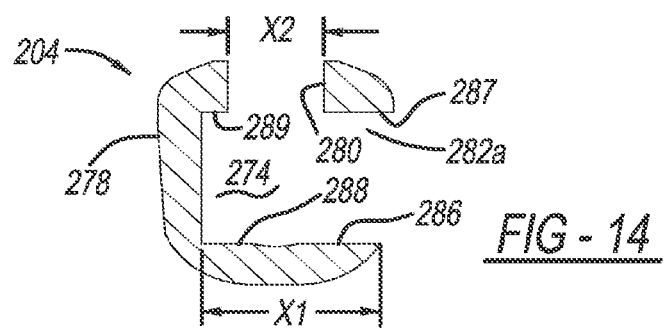
FIG. 14 is a cross-sectional view taken along the line 14-14 of FIG. 13.
Figure 23:
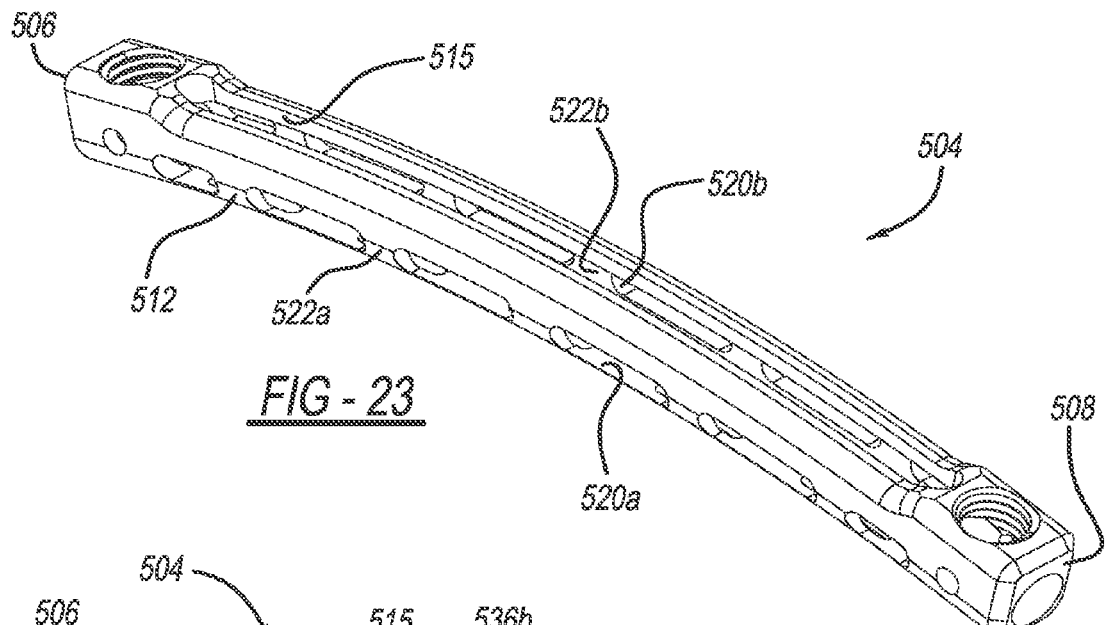
FIG. 23 is a perspective view of another connector of the system of FIG. 8.

With reference to FIGS. 8 through 14, the connector 204 may extend longitudinally between a first end 270 and a second end 272, and may include a channel or passage 274 in which a portion of the first rod 12 and a portion of the second rod 14 is positioned. The passage 274 may extend between the first rod opening 26 and the second rod opening 28. As illustrated in FIG. 14, in one configuration the passage 274 defines a generally rectangular cross-sectional shape. It will be appreciated, however, that the passage 274 may include other cross-sectional shapes within the scope of the present disclosure (e.g., round, hexagonal, elliptical, etc.)

The connector 204 may also include first and second sidewalls 276, 278 and an elongated opening or slot 280. The first and second sidewalls 276, 278 may extend between the first and second ends 270, 272. The elongated slot 280 may extend longitudinally between the first and second sidewalls 276, 278 and open into and communicate with the passage 274.

Figure 10B:
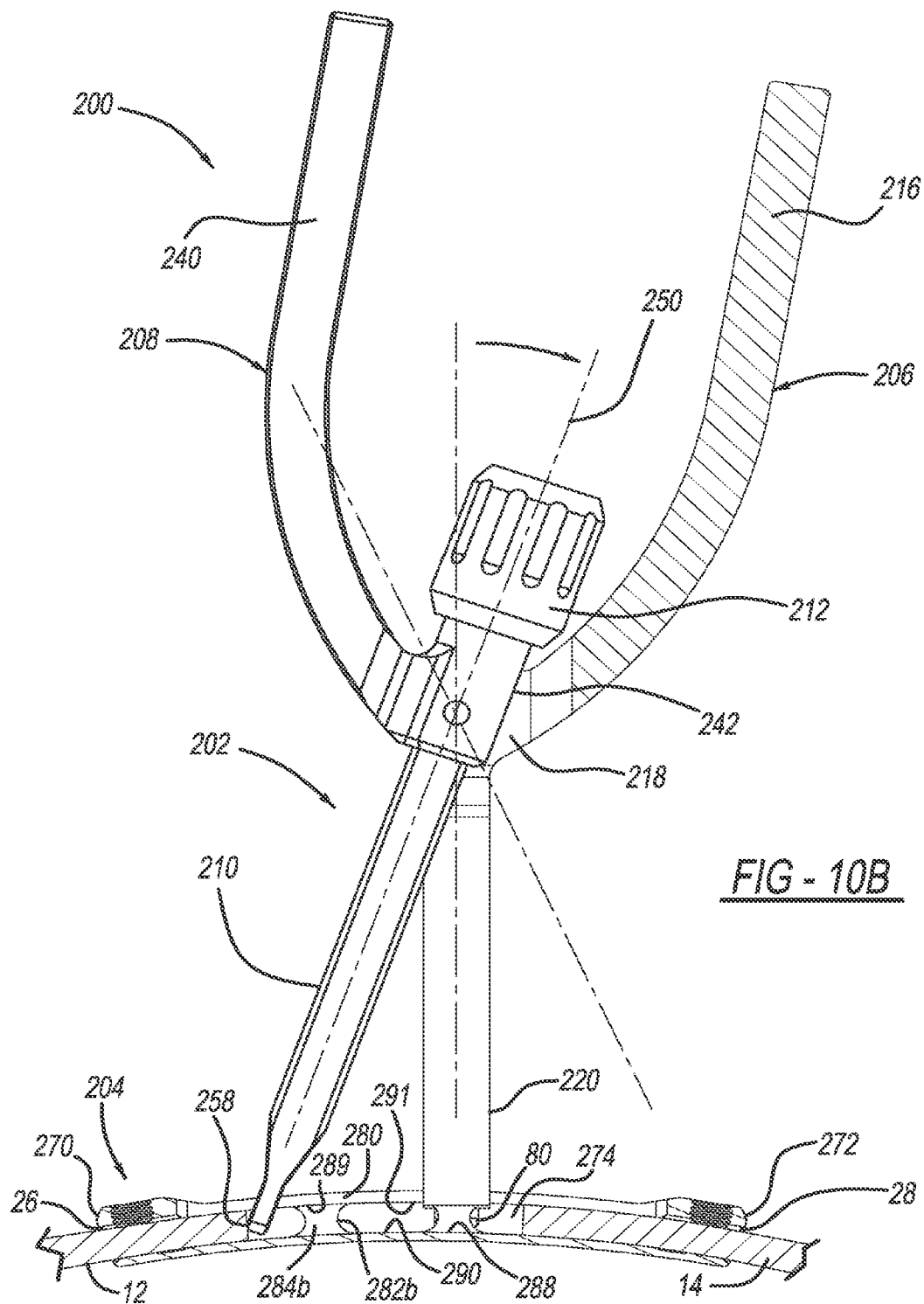
FIG. 10B is a cross-sectional view taken along the line 10A-10A of FIG. 9, the system shown in a second position.
Figure 11:
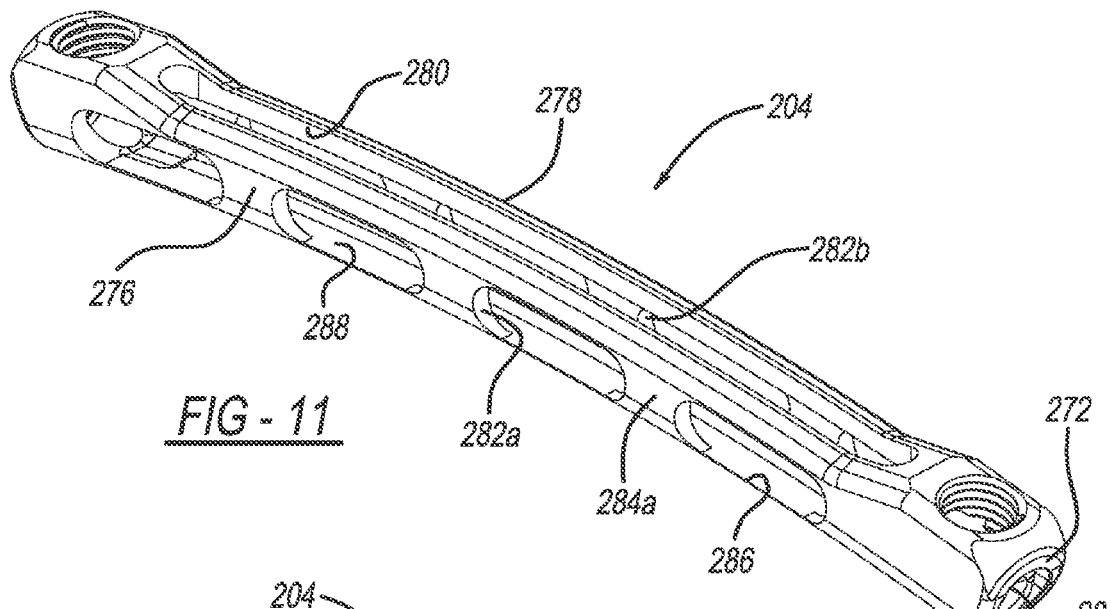
FIG. 11 is a perspective view of a connector of the system of FIG. 8.
Figure 12:
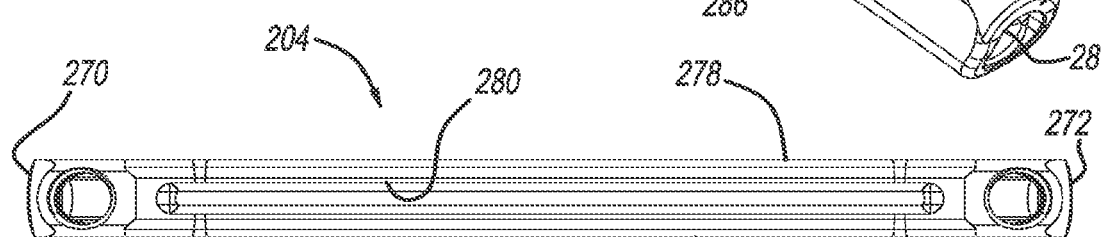
FIG. 12 is a top view of the connector of FIG. 11.

The first and second sidewalls 276, 278 may include a plurality of spaced apart slots 282a, 282b, respectively, oriented along the length of the connector 204 between the first and second ends 270, 272. The slots 282a in the first sidewall 276 may be laterally offset from, and overlap, the slots 282b in the second sidewall 278. In this regard, as illustrated in FIG. 13, the first sidewall 276 may define a bridge 284a extending between consecutive slots 282a. The bridge 284a may be laterally aligned with the slot 282b. Similarly, a bridge 284b extending between consecutive slots 282b may be laterally aligned with the slot 282a. As illustrated in FIGS. 13 and 14, a lower surface or edge 286 of the slots 282a may define, or otherwise be coplanar with, a bottom surface 288 of the passage 274, and an upper surface or edge 287 of the slots 282a may define, or otherwise be coplanar with, a top surface 289 of the passage 274. Similarly, a lower surface or edge 290 of the slots 282b may define, or otherwise be coplanar with, the bottom surface 288 of the passage 274, and an upper surface or edge 291 of the slots 282b may define, or otherwise be coplanar with, the top surface 289 of the passage 274 (FIG. 10B). In this regard, as illustrated, the slots 282a and the slots 282b may define an arcuately extending pattern. Specifically, each of the slots 282a, 282b may extend arcuately, and a group of slots 282a, 282b may extend in, or otherwise collectively define, an arc. As will be explained in more detail below, the arcuate nature or construct of the individual slots 282a, 282b and/or the group of slots 282a, 282b can allow for the construction of an arcuate or curved connector 204 having an arcuate or curved passage 274, while also allowing for the construction of the opening or slot 280 having a width X2 that is less than a width of the passage 274.

With reference to FIG. 14, a method of manufacturing the connector 204 may include machining the passage 274. Specifically, a milling or other cutting tool (not shown) may be used to form each of the slots 282a and 282b to define the passage 274. The slots 282a, 282b may be milled to a depth X1. A milling or other cutting tool (not shown) having the width X2 that is less than the depth X1, and less than a diameter or width of the first and second rods 12, 14, may be used to form the slot 280. The width X2 ensures that the first and second rods 12, 14 are secured within the passage 274 and cannot exit the slot 280.

Operation of the system 200 will now be described in more detail. The anchor 202 may be coupled to the connector 204 such that the first and second arms 60, 62 engage the slots 282a, 282b, respectively. Specifically, in one configuration, the projections 80 on the first arm 60 may engage the slot 282a, and the projections 80 on the second arm 62 may engage two of the slots 282b, such that the projections 80 on the second arm 62 are disposed on opposite sides of the bridge 284b. Similarly, in another configuration, the projections 80 on the first arm 60 may engage two of the slots 282a, and the projections 80 on the second arm 62 may engage the slot 282b, such that the projections 80 on the first arm 60 are disposed on opposite sides of the bridge 284a.

With the first and second arms 60, 62 engaging the slots 282a, 282b, respectively, the distal end 258 of the distracting member 210, including the tip 264, may be disposed within the passage 274 and/or the slot 280. In this regard, the user may rotate the adjustment member 212 such that the threaded portion 254 of the aperture 266 threadably engages the threaded portion 260 of the distracting member 210, to allow the distracting member 210 to extend within the passage 274 and/or the slot 280.

The second actuating member 208 may be pivoted about the hinge 244 relative to the first actuating member 206 by squeezing or otherwise moving the handle portion 216 relative to the handle portion 240. Pivoting the second actuating member 208 relative to the first actuating member 206 may cause the distracting member 210 to enter, and/or articulate within, the central passage 224. As the distracting member 210 articulates within the central passage 224, the distal end 258 of the distracting member may engage and move the first and/or second rod 12, 14 relative to the connector 204. In this regard, applying a force on the handle portions 216, 240 may cause the distracting member 210 to produce a corresponding force on one of the first and second surgical rods 12, 14 to distract the first and/or second surgical rod 12, 14 relative to the other of the first and second surgical rod 12, 14 and/or relative to the connector 204. As the distracting member 210 further articulates within the central passage 224, the distal end 258 of the distracting member 210 may disengage from the first and/or second rod 12, 14. Specifically, as the distracting member 210 follows an arcuate path 296 (FIGS. 10A and 10B), the distracting member 210 may exit the connector 204 through the slot 280. To re-engage the distracting member 210 with the first and/or second rod 12, 14, the user may rotate the adjustment member 212, as described above, and thus allow the distracting member 210 to extend within the passage 274 and/or the slot 280 and contact the first and/or second rod 12, 14.

With reference to FIGS. 15 through 18, another configuration of a connector 304 is shown. The structure and function of the connector 304 may be substantially similar to that of the connector 204 illustrated in FIGS. 8 through 14, apart from any exceptions described below and/or shown in the Figures. Therefore, the structure and/or function of similar features will not be described again in detail, and like reference numerals may be used to describe like features and components.

The connector 304 may extend longitudinally between a first end 306 and a second end 308, and may include a channel or passage 310 and a slot 312. The passage 310 may be defined by a concave sidewall of the connector 304. As illustrated in FIG. 18, in one configuration, the passage 310 may define a substantially circular cross section, and may extend between the first and second ends 306, 308. A portion of the first rod 12 and a portion of the second rod 14 may be positioned within the passage 310. The slot 312 may extend longitudinally between a first end 314 and a second end 316. A central portion of the slot 312 may be defined by substantially parallel sidewalls 318a, 318b. The first and second ends 314, 316 of the slot 312 may be substantially circular.

A method of forming the passage 310 and the slot 312 may include extending a milling or other cutting tool 320 into the connector 304. The cutting tool 320 may include a first portion 322 defining a diameter or width X3 and a second portion 324 defining a diameter or width X4 that is less than the width X3. The cutting tool 320 may be inserted into the connector 304 to create either or both of the first and second ends 314, 316. As the cutting tool 320 moves longitudinally between the first and second ends 314, 316, the first portion 322 may cut, or otherwise form, the passage 310 having the width X3, while the second portion 324 cuts, or otherwise forms, the slot 312 having the width X4. The widths X3, X4 can ensure that the first and second rods 12, 14 are slidably received within the passage 310 without exiting the slot 312.

With reference to FIGS. 19 through 22, another configuration of a connector 404 is shown. The structure and function of the connector 404 may be substantially similar to that of the connector 204 illustrated in FIGS. 8 through 14 and the connector 304 illustrated in FIGS. 15 through 18, apart from any exceptions described below and/or shown in the Figures. Therefore, the structure and/or function of similar features will not be described again in detail, and like reference numerals may be used to describe like features and components.

The connector 404 may extend longitudinally between a first end 406 and a second end 408, and may include a channel or passage 410 and a slot 412. The connector 404 may also include first and second sidewalls 414, 416 extending between the first and second ends 406, 408. The first and second sidewalls 414, 416 may include a plurality of spaced apart slots 418a, 418b, respectively, oriented along the length of the connector 404 between the first and second ends 406, 408. The slots 418a in the first sidewall 414 may be laterally offset from, and overlap, the slots 418b in the second sidewall 416. In this regard, as illustrated in FIG. 18, a bridge 420a extending between consecutive slots 418a may be laterally aligned with the slot 418b. Similarly, a bridge 420b extending between consecutive slots 418b may be laterally aligned with the slot 418a. As illustrated in FIG. 22, an upper surface or edge 422 of the slots 418a may define, or otherwise be coplanar with, an upper surface 424 of the passage 410. Similarly, an upper surface or edge 426 of the slots 418b may define, or otherwise be coplanar with, the upper surface 424 of the passage 410 and with the upper edge 422 of the slots 418a. A height H1 of the first and second slots 418a, 418b may be less than a height H2 of the passage 810. The height H1, that is less than the height H2, can improve the strength and rigidity of the connector 404. As noted above, in other respects, the slots 418a, 418b may be substantially similar to the slots 282a, 282b.

With reference to FIGS. 23 through 26, another configuration of a connector 504 is shown. The structure and function of the connector 504 may be substantially similar to that of the connectors illustrated and described herein, apart from any exceptions described below and/or shown in the Figures. Therefore, the structure and/or function of similar features will not be described again in detail, and like reference numerals may be used to describe like features and components.

Figures 26, 27:
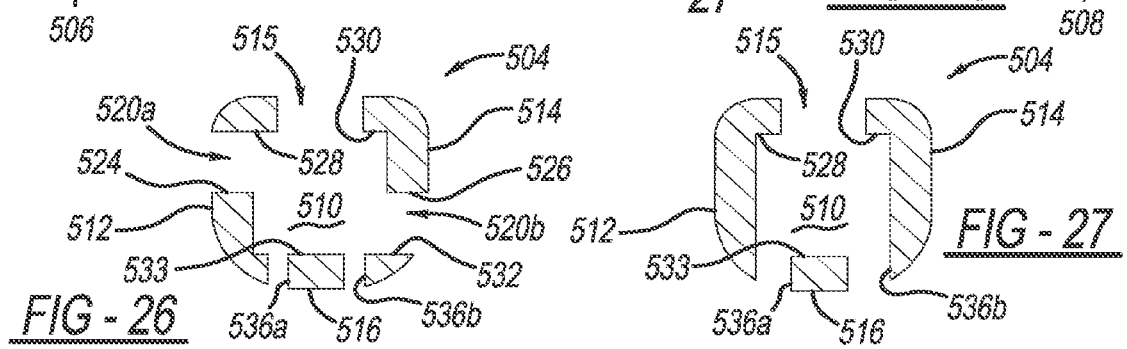
FIG. 26 is a cross-sectional view taken along the line 26-26 of FIG. 25.
FIG. 27 is a cross-sectional view taken along the line 27-27 of FIG. 25.

The connector 504 may extend longitudinally between a first end 506 and a second end 508, and may include a channel or passage 510 in which a portion of the first rod 12 and a portion of the second rod 14 is positioned. As illustrated in FIG. 26, in one configuration the passage 510 defines a generally rectangular cross-sectional shape.

The connector 504 may be at least partially defined by first and second sidewalls 512, 514, a bottom wall 516. The first and second sidewalls 512, 514 may define an elongated opening or slot 515 therebetween. The first and second sidewalls 512, 514 may extend between the first and second ends 506, 508. The bottom wall 516 may extend between and connect the first and second sidewalls 512, 514. The elongated slot 515 may extend longitudinally between the first and second sidewalls 512, 514 and open into and communicate with the passage 510.

Figure 25:
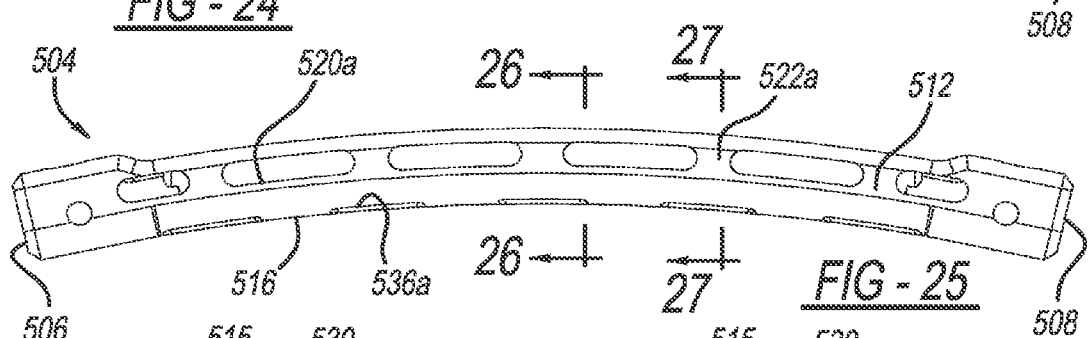
FIG. 25 is a side view of the connector of FIG. 23.

The first and second sidewalls 512, 514 may include a plurality of spaced apart slots 520a, 520b, respectively, oriented along the length of the connector 504 between the first and second ends 506, 508. The slots 520a may be laterally aligned with the slots 520b in the second sidewall 514. In this regard, as illustrated in FIG. 25, a first bridge 522a extending between consecutive slots 520a may be laterally aligned with a second bridge (not shown) extending between consecutive slots 520b. As illustrated in FIG. 26, in some configurations a lower surface or edge 524 of the slots 520a may define, or otherwise be coplanar with, an upper surface 526 of the slots 520b, and an upper surface or edge 528 of the slots 520a may define, or otherwise be coplanar with, an upper surface 530 of the passage 510. In addition, a lower surface or edge 532 of the slots 520b may define, or otherwise be coplanar with, a lower surface 533 of the passage 510.

Figure 24:
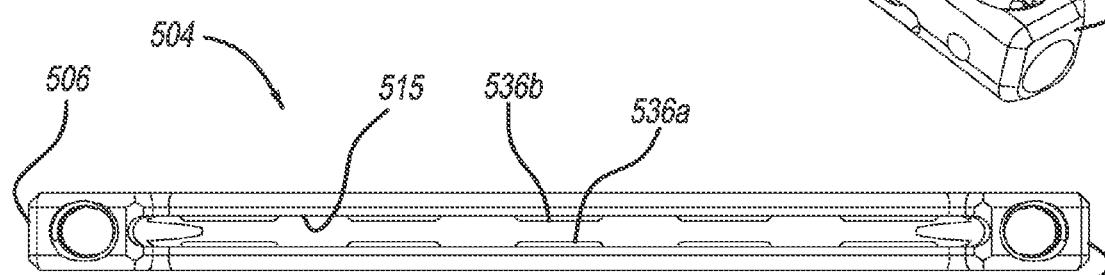
FIG. 24 is a top view of the connector of FIG. 23.

The bottom wall 516 may include a first and second plurality of slots 536a, 536b. As illustrated in FIG. 24, the first and second plurality of slots 536a, 536b may each define a substantially linear pattern extending longitudinally between the first and second ends 506, 508 of the connector 504. The first plurality of slots 536a may be laterally aligned with the second plurality of slots 536b and with the first bridge 522a (FIG. 25). The second plurality of slots 536b may be laterally aligned with the second bridge 522b.

A method of manufacturing the connector 504 may include machining the passage 510. Specifically, a milling or other cutting tool (not shown) may be used to form each of the slots 520a and 520b, and thus define at least a portion of the top and bottom surfaces 530, 533 respectively, of the passage 510. Similarly, a milling or other cutting tool (not shown) may be used to form each of the slots 536a, 536b, and thus define a remaining portion of the top surface 530 of the passage 510. A milling or other cutting tool (not shown) may also be used to form the elongated slot 515, and to at least partially define the lower surface 533 of the passage 510. It will be appreciated that aligning the slots 536a, 536b with the bridges 522a, 522b, respectively, allows for the manufacture of a continuous passage 510 along the length of the connector 504. In this regard, with reference to FIGS. 26 and 27, it will also be appreciated that the slots 536a, 536b and the slots 520a, 520b can define the width of the sidewalls of the passage 510. Accordingly, the slot 515 can have a width that is less than the width of the sidewalls of the passage 510. The width of the slot 515 relative to the width of the sidewalls of the passage 510 ensures that the first and second rods 12, 14 are secured within the passage 510, and cannot exit the slot 515, in a similar manner as that described above with respect to connectors 204 and 304.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A surgical rod connector system comprising:
a surgical rod connector comprising:
a housing with first and second ends, each of the first and second ends adapted to receive a rod;
first and second sidewalls extending between the first and second ends;
a longitudinal passage extending between the first end and the second end and extending between the first and second sidewalls;
an opening in an exterior surface of the housing between the first and second sidewalls in communication with the longitudinal passage adapted to receive a distracting member at any location along a length of the opening, the opening extending uninterruptedly from a third end adjacent the first end to a fourth end adjacent the second end; and
an anchor mechanism comprising:
first and second arms configured to engage the first and second sidewalls, respectively, of the surgical rod connector at one of a plurality of discrete positions spaced along the first and second sidewalls;
wherein the anchor mechanism further comprises a body, wherein the first and second arms are rotatably connected to the body.

2. The system of claim 1, wherein the surgical rod connector further comprises a plurality of slots disposed along the first and second sidewalls, the plurality of slots corresponding to the plurality of discrete positions, wherein the plurality of slots includes pairs of slots disposed opposite each other on opposite sidewalls.

3. The system of claim 2, wherein:
the surgical rod connector further comprises first and second closure mechanisms located between the first and second ends and the opening, respectively; and
wherein the opening is located between the first and second closure mechanisms.

4. The system of claim 3, wherein:
the first and second closure mechanisms each comprises threaded set screws configured to be mounted within first and second apertures, respectively; and
the housing further comprises first and second rod openings located proximate the first and second ends.

5. The system of claim 1, wherein each of the first and second arms comprises:
a first end for engaging one of the slots;
a second end; and
a bore located between the first end and the second end for rotatably coupling each arm to the body.

6. The system of claim 5, wherein the anchor mechanism further comprises a locking mechanism configured to be rotated between the second ends to immobilize rotation of the first and second arms.

7. The system of claim 5, wherein:
the plurality of slots are positioned between bridges extending along the first and second sidewalls, wherein bridges on the first sidewall are longitudinally offset from bridges on the second sidewall; and
each of the first ends comprises a pair of projections configured to be inserted into one of the plurality of slots, wherein:
a distance between projections in each pair of projections is equal to a width of a bridge and an outside width of a pair of projections is equal to a width of a slot.

8. The system of claim 1, wherein the anchor mechanism further comprises the distracting member, the distracting member being rotatable relative to the body along an arc at an axis of rotation, wherein the distracting member is insertable into the longitudinal passage through the opening.

9. The system of claim 8, wherein the anchor mechanism further comprises an adjustment member configured to adjust a height of the distracting member relative to the axis of rotation.

10. The surgical rod connector system of claim 1, wherein the third end is located a first distance from the first end and the fourth end is located a second distance from the second end, the first distance and the second distance being equal to each other.

11. A surgical rod connector system comprising:
a housing with first and second ends, each of the first and second ends adapted to receive a rod, the housing comprising:
first and second sidewalls extending between the first and second ends;
a top wall extending between and connecting the first and second sidewalls;
a longitudinal passage extending between the first end and the second end and extending between the first and second sidewalls;
an opening within the top wall extending between the first and second sidewalls in communication with the longitudinal passage from proximate the first end to proximate the second end;
first and second closure mechanisms disposed on opposite sides of the opening and proximate the first and second ends, respectively;
a bottom wall extending between and connecting the first and second sidewalls, the bottom wall extending parallel to the top wall; and
a plurality of slots disposed along the first and second sidewalls to receive an anchor mechanism at one of a plurality of discrete positions spaced along the first and second sidewalls;
wherein the slots disposed along the first sidewall extend along a first plane and the slots disposed along the second sidewall extend along a second plane that opposes the first plane; and an anchor mechanism comprising:
first and second arms configured to engage the first and second sidewalls, respectively, of the surgical rod connector at one of a plurality of discrete positions spaced along the first and second sidewalls;
wherein the anchor mechanism further comprises a body, wherein the first and second arms are rotatably connected to the body.

12. The surgical rod connector system of claim 11, wherein:
the housing extends arcuately between the first and second ends such that the longitudinal passage extends along an arcuate longitudinal trajectory; and
the plurality of slots are disposed along arcuate paths on the first and second sidewalls that follow the arcuate longitudinal trajectory of the longitudinal passage.

13. The surgical rod connector system of claim 11, wherein the housing is necked down between the first and second closure mechanisms.

14. The surgical rod connector system of claim 11, wherein:
a first height of the plurality of slots is less than a second height of the longitudinal passage; and
the plurality of slots are positioned closer to the opening than the bottom wall connecting the first and second sidewalls.

15. The surgical rod connector system of claim 11, wherein the plurality of slots are positioned between bridges extending along the first and second sidewalls, wherein bridges on the first sidewall are longitudinally offset from bridges on the second sidewall.

16. The surgical rod connector system of claim 11, further comprising:
a plurality of slots disposed within the bottom wall.

17. The surgical rod connector system of claim 11, wherein the slots disposed along the first sidewall extend along a first axis and the slots disposed along the second sidewall extend along a second axis, wherein the first axis and the second axis are equidistant from a surface of the housing into which the opening extends.

18. The surgical rod connector system of claim 11, wherein the plurality of slots are located on portions of the first and second sidewalls that are parallel to each other and perpendicular to a surface of the housing into which the opening extends.

* * * * *